United States Patent [19]
Danby et al.

[11] Patent Number: 4,533,350
[45] Date of Patent: Aug. 6, 1985

[54] PARENTERAL SOLUTION DELIVERY CONTROL SYSTEM

[75] Inventors: Hal C. Danby, Palo Alto; Carl Ritson, San Jose, both of Calif.

[73] Assignee: Anatros Corporation, San Jose, Calif.

[21] Appl. No.: 493,188

[22] Filed: May 10, 1983

[51] Int. Cl.³ .............................................. A61M 5/16
[52] U.S. Cl. .................................................... 604/253
[58] Field of Search .................. 604/65, 67, 122, 123, 604/245, 246, 251, 253, 256; 73/861.41

[56] References Cited

U.S. PATENT DOCUMENTS

| | | | |
|---|---|---|---|
| 3,563,090 | 2/1971 | Deltour | 604/253 |
| 4,038,982 | 8/1977 | Burke et al. | 604/253 |
| 4,105,028 | 8/1978 | Sadlier et al. | 604/253 |
| 4,181,130 | 1/1980 | Bailey | 604/253 |
| 4,244,365 | 1/1981 | McGill et al. | 604/123 |
| 4,261,388 | 4/1981 | Shelton | 604/253 |
| 4,328,801 | 5/1982 | Marx et al. | 604/65 |
| 4,346,606 | 8/1982 | Cannon et al. | 604/253 |
| 4,460,358 | 7/1984 | Somerville et al. | 604/245 |

FOREIGN PATENT DOCUMENTS 2830512  1/1980  Fed. Rep. of Germany ........ 604/65

OTHER PUBLICATIONS

IBM Tech. Bulletin, vol. 12, No. 5, Oct. 1969, p. 693.

Primary Examiner—C. Fred Rosenbaum
Assistant Examiner—Michelle N. Lester
Attorney, Agent, or Firm—William B. Walker

[57] ABSTRACT

A parenteral solution delivery control system for housing a drip chamber and detecting drops falling therethrough. One or more light sources are employed to provide light beam transverse to the drip chamber axis and covering the cross-section of the drip chamber so that drops falling therethrough, even when the drip chamber is tilted, break a light beam. A retention bar is provided to maintain the drip chamber in proper position and to break a light beam when the drip chamber is in position, thereby preventing operation of the device when not properly assembled. A liquid level control monitor is configured to provide an energized signal when the area of the drip chamber occupied by liquid during normal operation is filled with air as a consequence of the liquid level falling to an abnormal level.

5 Claims, 7 Drawing Figures

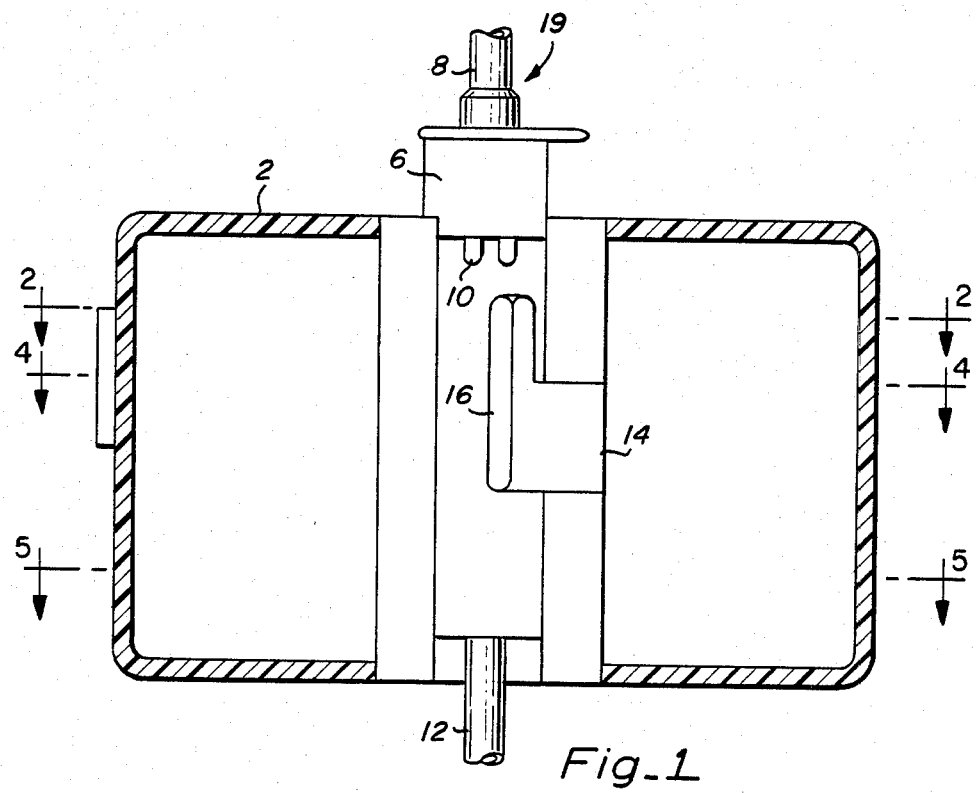
Fig_1
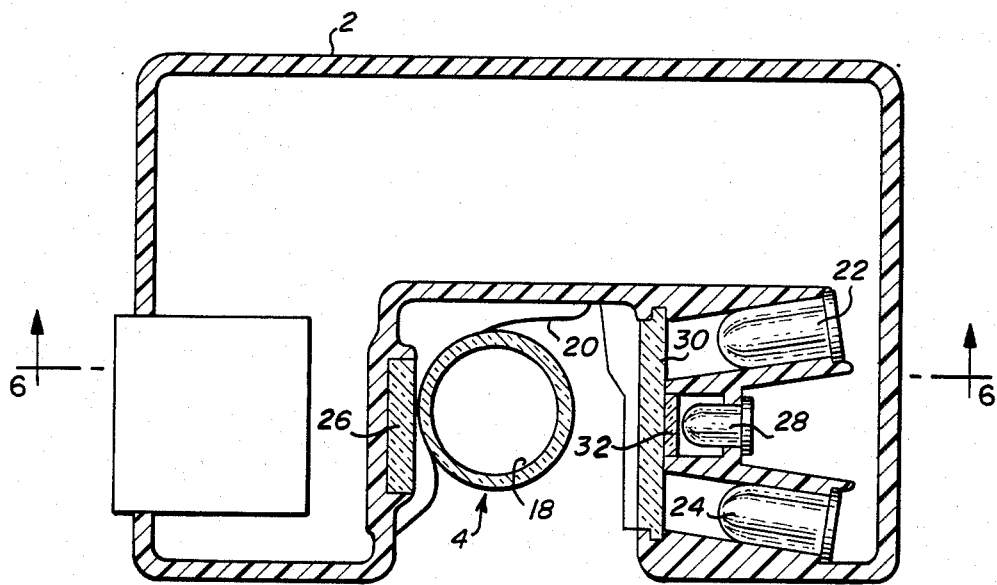
Fig_2

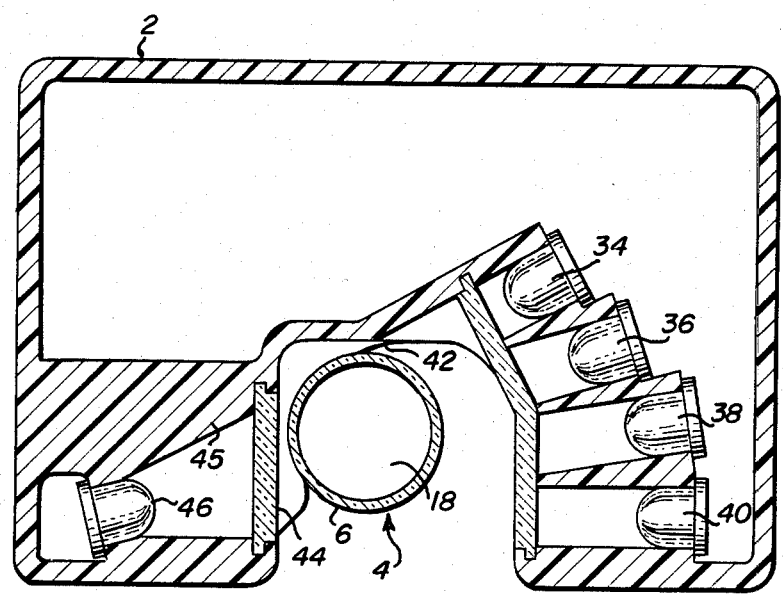
Fig_3
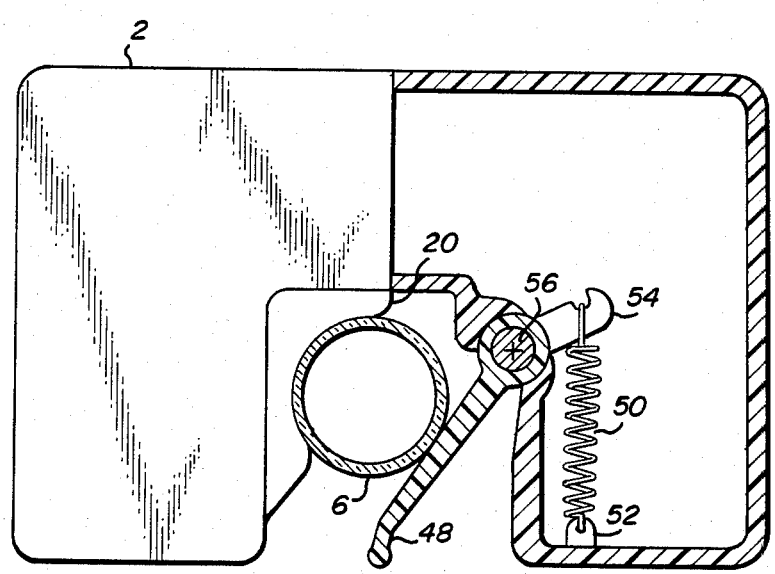
Fig_4

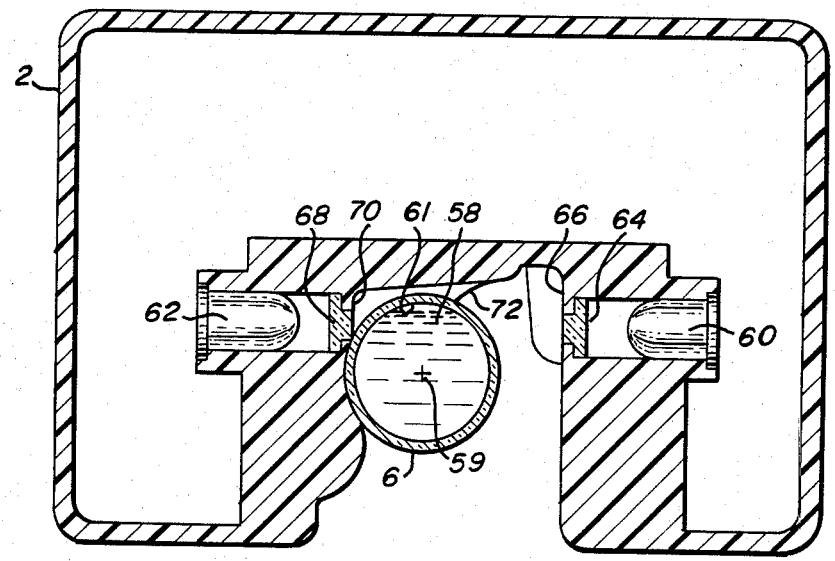
Fig_5
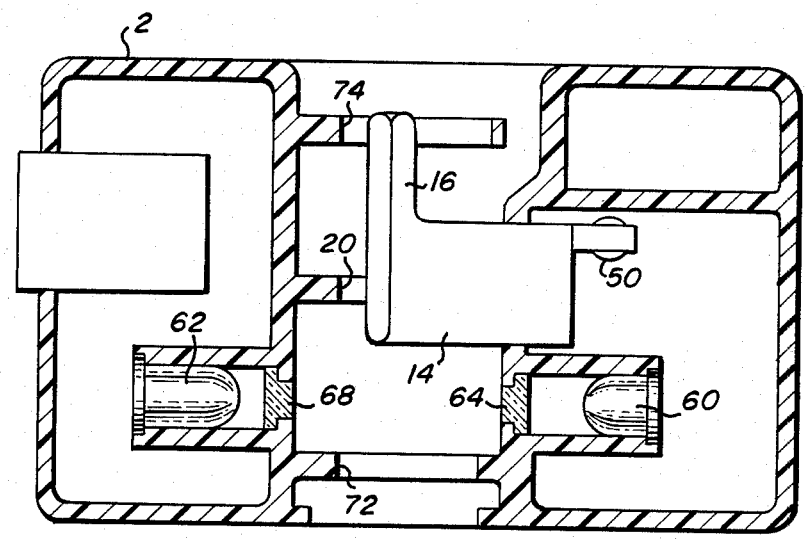
Fig_6
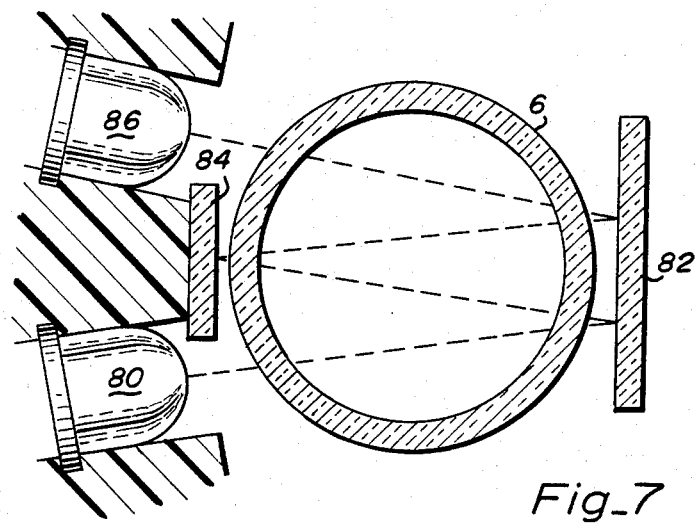
Fig_7

PARENTERAL SOLUTION DELIVERY CONTROL SYSTEM

FIELD OF THE INVENTION

This invention relates to an apparatus for administering parenteral solutions to medical patients. In particular, this application is directed to an improved apparatus for delivering solutions at precise rates and with improved reliability and safety.

BACKGROUND OF THE INVENTION

DESCRIPTION OF THE PRIOR ART

Infusion delivery systems for delivering liquid to a patient from more than one solution source have been previously known. The most common systems use gravity flow and manually adjustable tubing clamps or pinch valves. They may employ a variety of valves and junctions to control flow at the desired rate and sequence. Examples of such systems are described in U.S. Pat. Nos. 3,886,937; 4,034,754; 4,114,617; 4,219,022; 4,223,695; 4,236,515; 4,237,879; 4,237,880; 4,250,879; 4,252,116; 4,256,104; 4,256,105; and 4,258,712. Dual delivery systems relying on electronic flow control means are described in U.S. Pat. No. 4,094,318, for example.

Automatic flow control systems relying on a drop counter which measures the frequency of drop fall through a drip chamber have been previously known. In general, a light beam from a lamp to a light detector is positioned so that it is interrupted by drops falling through a drip chamber. The frequency of the breaking of the light beam and/or the time lapse between drops breaking the light beam are directly proportional to the flow rate and are used to determine adjustments to be made to a flow control valve to change flow to the desired rate. Examples of systems comprising drop counters and control systems responsive thereto are described in U.S. Pat. Nos. 3,163,179; 3,601,124; 3,886,937; 4,038,982; 4,314,567.

SUMMARY AND OBJECTS OF THE INVENTION

It is an object of this invention to provide a system for precise monitoring drop rates in a drip chamber which operates accurately even when the central axis of the drip chamber is not precisely vertical.

It is a further object of this invention to provide an improved system for measuring drops falling through a drip chamber wherein a failure to properly engage the drip chamber in the detector can be automatically detected.

A still further object of this invention is to provide a liquid level monitor which signals when the level of liquid in a drip chamber falls below the level of normal operation or rises above the level of normal operation.

The parenteral solution delivery control system of this invention comprises a housing having a recess for receiving a drip chamber and having a drop detection zone corresponding to a plane intermediate the drop former and retained liquid level of a drip chamber positioned in the recess. The plane is transverse to the central axis of the drip chamber. A light path drop detector means is provided defining a plurality of light paths substantially covering the area of said plane circumscribed by the wall of the drip chamber positioned in the recess. The drop detector means includes a light detector and at least one light source defining a plurality of light paths therebetween. In one embodiment of this invention, the light path drop detector means includes at least four light sources, the central axis of each being aligned with a drop detector, and being spaced apart to form partially overlapping light paths substantially covering said area of the circumscribed plain. In an alternate embodiment, two light sources and a light detector are positioned on one side of the drip chamber zone and a reflector is positioned on the opposite side thereof whereby the light paths from the light sources to the reflector and from the reflector to the light detector at least partially overlap and substantially cover said area of the circumscribed plain. In a third embodiment a single light source, a single light detector and a first reflector are spaced apart on one side of a drip chamber zone and a second reflection is positioned on the opposite side, the elements aligned to provide overlapping light paths from the light source to the second reflector, from the second reflector to the first reflector, from the first reflector to the second reflector and from the second reflector to the detector.

The parenteral solution delivery control system of this invention also comprises a housing having a vertical support surface in a cavity defining a drip chamber zone, a bar means pivotly connected to the housing, and spring biased and positioned to swing toward the support surface to bear against the external surface of a drip chamber positioned against said support surface, and when no drip chamber is in the cavity, to swing into the drip chamber zone. The bar means has a deflector for breaking a light path between a light source and a light detector when the bar swings into the drip chamber zone.

A still further embodiment of the parenteral solution delivery control system of this invention comprises a housing having a cavity therein for receiving a drip chamber having a circular cross-section, a liquid retention zone in the drip chamber zone corresponding to a zone occupied by liquid in normal operation of a drip chamber. A liquid level detector means is positioned to detect when the liquid retention zone is occupied by air. The liquid level detection means comprises a light emitting means and a light detector means, the light emitting means including a light source, and means positioned for directing light from the light source in a narrow path through the drip chamber in the liquid retention zone, the light path being positioned between the central axis of the drip chamber and the edge of the drip chamber. With this orientation, the light follows a focused path when the liquid retention zone is filled with transparent liquid, is blocked when the liquid retention zone is filled with opaque liquid, and is unfocused when the liquid retention zone is filled with air. A light detector means including a light detector and means directing unfocused light to the detector but blocking passage of focused light to the detector is provided, whereby, the detector is energized when the liquid retention zone is filled with air but is unenergized when the liquid retention zone is filled with transparent or opaque liquid. In one embodiment a light emitter means and detector means are provided above the normal liquid level to signal when the liquid level rises to above a maximum normal level. The light emitter means includes a path defining means directing a light path positioned between the central axis of the drip chamber and the edge of the drip chamber. A light detector and light blocking means are positioned to block focused beam light and prevent it from reaching the detector when the liquid level rises to above the maximum normal level but permitting unfocused or diffused beam light to reach the detector when the liquid level is below the normal maximum level.

BRIEF DESCRIPTION OF THE DRAWINGS

FIG. 1 is a frontal view of the parenteral solution delivery control system of this invention.

FIG. 2 is a cross-sectional view of the parenteral solution delivery control system of this invention taken along the line 2—2 in FIG. 1 and showing the drop detector assembly.

FIG. 3 is a cross-sectional view of an alternate embodiment of the parenteral solution delivery control system of this invention taken along the line 2—2 in FIG. 1.

FIG. 4 is a partial cross-sectional view of the parenteral solution delivery control system of this invention taken along the line 4—4 in FIG. 1 and showing the spring biased bar assembly.

FIG. 5 is a cross-sectional view of the parenteral solution delivery control system of this invention taken along the line 5—5 in FIG. 1 and showing the liquid level monitoring components.

FIG. 6 is a cross-sectional view of the parenteral solution delivery control system of this invention taken along the line 6—6 in FIG. 2 and showing the drip chamber retention bar and the liquid level monitoring components.

FIG. 7 is a schematic representation of an alternate drop detector configuration using a single light emitter, single light detector and opposed reflectors to generate a plurality of overlapping light paths.

DETAILED DESCRIPTION OF THE INVENTION

Referring to FIG. 1, a frontal view of the parenteral solution delivery control system of this invention is shown. This control system detects drops falling through a drip chamber, the drop rate indicating the parenteral solution flow rate through the system. This drop detector can be used in conjunction with a variety of flow control systems which are capable of modifying the flow rate in response to the detected drop rate. Suitable control systems are known in the art. Improved control systems are described in commonly assigned, copending applications Ser. No. 431,312 filed Sept. 30, 1982 directed to a "Parenteral Valve Assembly", application Ser. No. 480,527 filed Mar. 30, 1983 directed to a "Dual Source Parenteral Infusion Apparatus" and application Ser. No. 493,182 filed 5/10/83 (filed concurrently herewith) entitled "Pinch Valve Assembly", (ANA-10). The drop detector assembly of this invention is particularly suitable for use with pinch valve type flow control monitors and as flow control monitors for secondary fluids.

In the frontal view shown in FIG. 1, the housing 2 has a housing recess 4 in which a drip chamber 6 can be supported. Any standard type of drip chamber can be used. The drip chamber 6 has a sharp pointed inlet conduit 8 for penetrating the seal of a parenteral solution container, a drop former 10 which forms liquid into regularly sized droplets, and outlet tubing 12. The drip chamber is held against supports (not shown) by a spring biased bar 14 having a light beam deflector 16.

FIG. 2 is a cross-sectional view of the parenteral solution delivery control system of this invention taken along the line 2—2 in FIG. 1. The housing 2 has a recess 4 within which the drip chamber 6 is positioned. The drip chamber is held against the drip chamber support 20. The light sources 22 and 24 can be light emitting diodes pointing toward the reflector 26 at an angle which directs the reflected light beam toward the light detector 28. The light from each light emitting diode 22 and 24 crosses a plane transverse to the central axis of the drip chamber. The paths impinge upon and are reflected by the reflector 26 to paths which again cross the circular area 18 defined by the walls of the drip chamber 6. The light beams are then directed to the transparent plate 30 and through lens 32 to the light detector 28. The four light paths across the circular area 18 overlap and completely cover the area. Any drop falling through area 18 will interrupt at least one of these light beams, and the voltage generated by the light detector 28 will fluctuate as a result of the drop falling. With this arrangement, a light beam will be broken by a falling drop even when the housing is tilted or when the drip chamber axis is not precisely vertically aligned.

In devices having a single light path through the zone, malfunctions frequently occur when the drip chamber is not vertically aligned, the falling drops missing the single light path.

FIG. 3 is an alternate embodiment shown in cross-sectional view taken along the line 2—2 in FIG. 1. In this embodiment, four light sources such as the four light emitting diodes 34, 36, 38 and 40 are oriented to form light beams which overlap in the plane 18 of a drip chamber 6 defined by the drip chamber wall 18. The drip chamber 6 is supported against support surface 42. The light beams pass through transparent window 44 and impinge on the light detector 46. The four light sources are oriented to direct light on the light detector 46 and are spaced apart to form partially overlapping light paths substantially covering the area 18.

Light emitting diode 34 performs an additional function in combination with detector 46. The cross-sectional planar area defined by the drip chamber wall 18 is above the normal maximum liquid surface level, and this zone is normally filled with air. The diffused and unfocused light beam from emitter 34 is detected by the detector 46. However, if the liquid level rises to include this plane, this light beam is blocked. Opaque liquid would block the beam directly. Transparent liquid would convert the cylindrical drip chamber to a cylindrical, convex lens which focuses the light beam onto opaque plastic 45 blocking the beam. The emitters 34, 36, 38 and 40 can be energized sequentially in 3 microsecond pulses, and the failure of the emitter 34 to stimulate a detector voltage for a selected lapsed time, for example one second, can be used to signal an alarm and terminate liquid flow.

FIG. 4 is a partial cross-sectional view of the parenteral solution delivery control system of this invention taken along the line 4—4 in FIG. 1. This view shows the drip chamber retention bar. The drip chamber 6 is supported against the surface of the drip chamber support 20, held in place by pressure from the spring biased bar 48. A spring 50 connected to the housing projection 52 on one end and to a bar projection 54 causes the retention bar 48 to pivot clockwise about the axis 56 in the direction toward the drip chamber support 20.

The retention bar 48 has an additional function. It is critically necessary that the insertion of the drip chamber in the drop counter be automatically confirmed for operation of the system. If the drip chamber 6 is not positioned in the housing 2, the bar 48 is pivoted to the extreme clockwise position, that is, until it bears against the drip chamber support 20. Referring to FIG. 1, in this extreme position the light deflector 16 will block a light path from the light emitting diode 24 (FIG. 2) or diode 40 (FIG. 3), thereby signaling that the drip chamber is not in its proper position. This unfluctuating signal can be used to signal an alarm or prevent operation of the system.

FIG. 5 is a cross-sectional view of the parenteral solution delivery control system of this invention taken along the line 5—5 in FIG. 1. The liquid level control components of the device are shown. A drip chamber 6 is positioned against a drip chamber support 72 in the housing 2. This section is taken at a level which is below the surface of normal liquid level in the bottom of the drip chamber 6, and the circular area 58 defined by the drip chamber wall in the plane of this section is normally filled with liquid, being in a liquid retention zone. A liquid level detector means is shown positioned to detect when the liquid retention zone is occupied by air. The liquid level detector comprises as a light source or light emitting diode 60 and a light detector 62. The light emitting diode 60 is positioned to direct light through the lens 64 positioned in the opaque mask 66 to form a narrow beam of light which passes through the liquid retention zone 58 between the central axis 59 and the drip chamber wall 61 in the drip chamber 6. The light detector system includes a light detector 62, a transparent lens 68 in an opening in the opaque mask 70 directing diffused light received by the lens 68 to the light detector 62. When the liquid retention zone is filled with transparent liquid, the wall of the drip chamber 6 and the liquid 58 form a cylindrical or convex lens which focuses the light beam onto the opposite wall of the housing in an area of the mask which does not have the lens 68. Therefore, when the liquid retention zone 58 is filled with transparent liquid, light from the beam does not reach the light detector 62. When the liquid retention zone is filled with an opaque liquid, the light beam is entirely blocked, and again, no light reaches the light detector 62. However, when the liquid retention zone 58 is filled with air (when the liquid level falls to an abnormal level in the drip chamber 6), the light beam is diffused or unfocused, and substantial light from the light beam impinges on the lens 68 and reaches the light detector 62. Thus, when the light detector 62 is energized, it indicates the presence of air in the liquid retention zone 58. This signal can be used to sound an alarm or terminate operation of the system.

FIG. 6 is a cross-sectional view of the parenteral solution delivery control system of this invention taken along the line 6—6 in FIG. 2. This view is shown without a drip chamber being in place to more clearly show elements of the structure. The bar 14 pivots about its axis 56 (FIG. 4) and when a drip chamber is not in place against the drip chamber supports 74, 20 and 72, the spring 50 biases the bar 14 so that it pivots until it contacts the drip chamber support structure. As described above, in this position, the deflector 16 is positioned in a light beam, the interruption thereof signaling that a drip chamber is not in place. This can be used to sound an alarm and terminating operation of the system. The liquid level monitor light emitting diode 60, light detector 62 and lenses 64 and 68 are also shown.

FIG. 7 is a schematic representation showing a still further embodiment of the drop detector of this invention. Light emitting diode 80 produces a light beam which passes through drip chamber 6, reflecting on the opposed reflecting surface 82. The reflected light beam (shown with arrows) passes through the drip chamber 6, impinging on reflecting surface 84. This produces a reflected beam which again crosses through the drip chamber 6, is reflected by reflector 82, passes through the drip chamber 6 to impinge on detector 86. The reflector 84 and the separation of opaque material 88 must be sufficiently close to the surface of the drip chamber wall to prevent significant reflective scattering of light from emitter 80 to diode 86 as a result of reflection by the wall surfaces of the drip chamber.

The invention claimed is:

1. A parenteral solution delivery control system comprising a housing having a vertical support surface means in a recess defining a drip chamber zone, a bar means pivotally connected to the housing, the bar means being spring biased and positioned to swing toward the support surface means about an axis parallel to the axis of a drip chamber positioned against the vertical support surface means to contact the external surface of such a drip chamber, and when no drip chamber is in the recess, to swing into the drip chamber zone, said bar means including a deflector means for blocking a light path between a light source and a light detector through said drip chamber zone when the bar swings into the drip chamber zone.

2. A parenteral solution delivery control system of claim 1 wherein the recess defines a drop detection zone corresponding to a plane intermediate a drop former and the normal surface level of retained liquid in a drip chamber, the plane being transverse to the central axis of a drip chamber if received therein, a light path drop detector means defining a plurality of light paths substantially covering the area of said plane which would be circumscribed by the walls of the drip chamber.

3. A parenteral solution delivery control system of claim 2 wherein the light path drop detector means includes a light detector and a plurality of light sources defining light paths therebetween.

4. A parenteral solution delivery control system of claim 3 wherein the light path drop detector means includes at least four light sources, the central axis of each being aligned with the light detector, and the light sources being spaced apart to form partially overlapping light paths substantially covering said area of the plane circumscribed by the walls of a drip chamber.

5. A parenteral solution delivery control system comprising a housing having a recess for receiving a drip chamber with a circular cross-section, a liquid retention zone in the drip chamber zone corresponding to a zone occupied by liquid in normal operation of the device, a liquid level detector means positioned for detecting when the liquid retention zone is occupied by air, the housing having a vertical support surface means in the recess defining the drip chamber zone, a bar means connected to the housing for pivotal movement about an axis substantially parallel to the axis of a drip chamber positioned in the recess against the vertical support surface means, the bar being spring biased and positioned to swing toward the support surface means to contact the external surface of such a drip chamber, and when no drip chamber is in the recess, to swing into the drip chamber zone, said bar means including a deflector means for blocking a light path between a light source and a light detector through said drip chamber when the bar swings into the drip chamber zone.

* * * * *